United States Patent [19]

Kingston et al.

[11] Patent Number: 5,633,283

[45] Date of Patent: May 27, 1997

[54] METHOD FOR TREATING MULTIPLE SCLEROSIS

[75] Inventors: Ann E. Kingston, Camberley, United Kingdom; Jill A. Panetta, Zionsville, Ind.

[73] Assignee: Eli Lilly and Company, Indianapolis, Ind.

[21] Appl. No.: 376,619

[22] Filed: Jan. 23, 1995

[51] Int. Cl.$^6$ ................................................ A61K 31/135
[52] U.S. Cl. ...................... 514/653; 514/658; 514/903
[58] Field of Search ............................... 514/903, 653, 514/658

[56] References Cited

U.S. PATENT DOCUMENTS

| | | | |
|---|---|---|---|
| 3,809,761 | 5/1974 | Lerner | 424/330 |
| 5,002,946 | 3/1991 | Manara et al. | 514/230.8 |
| 5,280,046 | 1/1994 | Lafferty et al. | 514/655 |

FOREIGN PATENT DOCUMENTS

| | | |
|---|---|---|
| 0042589 | 12/1981 | European Pat. Off. . |
| 0474403 | 3/1992 | European Pat. Off. . |

OTHER PUBLICATIONS

CA 118 : 122972.
CA 119 : 179176.
CA114:59941 (Abstract of Zdravookhr. Turkm. (1990), (9), 29–33, Lobzin et al.).
CA11:178020 (Abstract of PCT WO 8808424 (881103) 1988 McCall et al).
Chemical Abstracts 66 16925d (1967).
Chemical Abstracts 74 96312e(1971).
Chemical Abstracts 78 132326f (1973).
Chemical Abstracts 109 129047u (1988).
Chemical Abstracts 97 200429m (1982).
Chemical Abstracts 88 38847m (1978).
Chemical Abstracts 88 192135; (1978).
Chemical Abstracts 77 141203v (1972).
Chemical Abstracts 91 212411p (1979).
Chemical Abstracts 100 35563w (1984).
Chemical Abstracts 107 42468s (1987).
Chemical Abstracts 73 86385w (1970).

*Primary Examiner*—José G. Dees
*Assistant Examiner*—Mary C. Cebulak
*Attorney, Agent, or Firm*—Arleen Palmberg; Douglas J. Taylor; David E. Boone

[57] ABSTRACT

Provided is a method of treating multiple sclerosis employing certain phenol and benzamide compounds.

15 Claims, No Drawings

METHOD FOR TREATING MULTIPLE SCLEROSIS

BACKGROUND OF THE INVENTION

This invention provides a method of treating multiple sclerosis in mammals.

Multiple sclerosis was first described as a clinical entity in 1868. Clinically, it is a highly variable disease, which usually begins between the second and fifth decades of life. The most common signs of multiple sclerosis are sensory and visual motor dysfunction. In the chronic form the patient has periods of remission, but with each remission there is greater neurological dysfunction.

Macroscopically, multiple sclerosis involves lesions of 1 to 4 cm called plaques scattered throughout the white matter of the central nervous system. Microscopically, the disease is characterized by a breakdown of the nervous system's myelin sheath. There is also a loss of myelin basic protein in the area of the lesions.

The etiology and pathogenesis of multiple sclerosis remains obscure. Both chronic infectious agents and auto-immunity have been involved and, in fact, both might be important. Meanwhile, the need continues for safer, better calibrated drugs which will either slow the process of neurodegeneration associated with multiple sclerosis or even prevent such neurodegeneration altogether.

It is an object of this invention to provide a new method for treating multiple sclerosis, which method comprises administering a compound selected from among certain phenols and benzamides of the general formula

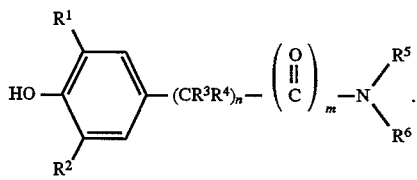

Such phenols and benzamides are known in the art and have been found to possess various utilities.

U.S. Pat. No. 3,305,483 discloses that certain phenols of the above formula can be used as an antioxidant for various substances such as gasoline, diesel fuel, heating oil, lubricating oil, asphalt, petroleum wax and high molecular weight hydrocarbon polymers. *Chemical Abstracts*, 97, 200429m (1982) teaches that 4-(2-dimethylaminoethyl)-2,6-di-t-butylphenol can be used as an antioxidant for jet aircraft fuel. European Patent Application 42,589 describes the use of various of the above phenols as antioxidants for polymeric norbornene type polymeric materials.

*Chemical Abstracts*, 88, 38847m (1978) discloses that 2,6-di-t-butyl-4-[N,N-bis(2-hydroxyethyl)aminomethyl] phenol can be used to increase the heat resistance of certain fibers. *Chemical Abstracts*, 88, 192135j (1978) teaches that 1-phenyl-4-(3,5-di-t-butyl-4-hydroxybenzyl)piperazine is a noncolorizing thermostabilizer for stress-stable polystyrene. 2-(3,5-Di-t-butyl-4-hydroxyphenyl)ethylmethylamine is described as being useful for improving the lightfastness of dyed polyester fibers in *Chemical Abstracts*, 76, 7362q (1972).

*Chemical Abstracts*, 77, 141203v (1972) teaches that 3-(dimethylamino)propylaminobis(4-methylene-2,6-di-t-butylphenol can be used to improve the aging resistance of diene rubber. *Chemical Abstracts*, 91 212411p (1979) describes a 1:1 pyrocatechol/4-[(di-methylamino)methyl]-2, 6-di-t-butylphenol complex which deactivates transition metals in rubber. N,N-dimethyl-3,5-di-t-butyl-4-hydroxybenzylamine is disclosed to be an effective polymerization inhibitor for styrene in *Chemical Abstracts*, 100, 35563w (1984). Chemical Abstracts, 107, 42468s (1987) discloses that 3-(4-hydroxy-3,5-di-t-butylphenyl)-1-aminopropane acetate or N-(4-hydroxy-3,5-di-t-butylbenzyl)-N-(β-aminoethyl)piperazine hydrochloride can be used to modify cation exchange resins so as to reduce the diffusive permeability of the resin membrane and increase its sodium ion transport properties.

Several of the phenols and benzamides of the general formula set forth above have also been found to possess various pharmacological activities. U.S. Pat. No. 5,281,623 discloses that such compounds can be used to treat inflammatory conditions and muscular dystrophy or prevent ischemia-induced cell damage. European Patent Application No. 474,403 teaches such compounds can be used to treat inflammatory bowel disease. U.S. Pat. No. 5,280,046 discloses that the above compounds can be used to treat Type I diabetes. U.S. Pat. No. 3,809,761 discloses that certain of the above phenols can be used to reduce mammalian plasma lipid levels. *Chemical Abstracts*, 73, 86385w (1970) and *Chemical Abstracts*, 66, 16925d (1967) teach that certain of the above phenols have anti-tumor activity. *Chemical Abstracts*, 74, 96312e (1971) discloses that (4-hydroxy-3, 5-di-t-butylbenzyl)methylamine hydrochloride increases the antioxidative activity of liver lipids, thereby increasing liver tissue regeneration following a partial hepatectomy. N-methyl-3,5-di-t-butyl-4-hydroxybenzylamine is said to be able to increase the rate of blood deoxygenation in *Chemical Abstracts*, 78, 132326f (1973). Finally, *Chemical Abstracts*, 109, 129047u (1988) discloses that certain benzamides of the above formula are useful for treating epilepsy and high blood pressure.

The phenols and benzamides employed in the method of the present invention have not heretofore been used to treat multiple sclerosis. The known activities of such compounds, as set forth above, in no way suggest the method of the present invention. Accordingly, an object of the present invention is to provide a new pharmacological use for certain known phenols and benzamides.

Other objects, features and advantages of the present invention will become apparent from the subsequent description and the appended claims.

SUMMARY OF THE INVENTION

This invention provides a method of treating multiple sclerosis in a mammal in need of such treatment which comprises administering to said mammal a therapeutically effective amount of a compound, or pharmaceutically acceptable salt thereof, of formula I

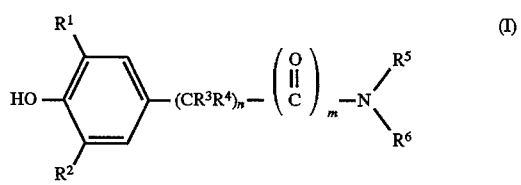

wherein:

$R^1$ and $R^2$ are each independently hydrogen, $C_1$–$C_6$ alkyl, $C_1$–$C_6$ alkoxy or

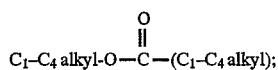

R³ and R⁴ are each independently hydrogen or $C_1$–$C_4$ alkyl;

n is an integer from 0 to 4, both inclusive;

m is 0 or 1; and

R⁵ and R⁶ are defined to be one of the following:

A) R⁵ and R⁶ are each independently hydrogen, $C_1$–$C_8$ alkyl, $C_3$–$C_8$ cycloalkyl, $C_2$–$C_8$ alkenyl, $C_2$–$C_8$ alkynyl, —$(CH_2)_q$$OR^7$, —$(CH_2)_q$$N(R^7R^8)$, —$(CH_2)_q$$SR^7$, —$(CH_2)_r$ napthyl or

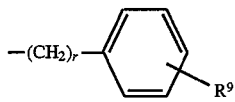

where q is an integer from 1 to 6, both inclusive, R⁷ and R⁸ are each independently hydrogen or $C_1$–$C_4$ alkyl, R⁹ is hydrogen, halo, $C_1$–$C_4$ alkyl, trifluoromethyl, hydroxy, amino, $C_1$–$C_4$ alkylamino, di($C_1$–$C_4$ alkyl)amino, phenylamino or diphenylamino, and r is an integer from 0 to 4, both inclusive;

B) one of R⁵ or R⁶ is as defined in (A) above and the other is

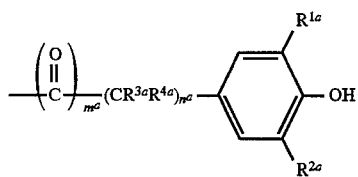

wherein $m^a$, $n^a$, $R^{2a}$, $R^{3a}$ and $R^{4a}$ are the same as m, n, R¹, R², R³ and R⁴, respectively; or C) R⁵ and R⁶, taken together with the nitrogen atom to which they are attached, form

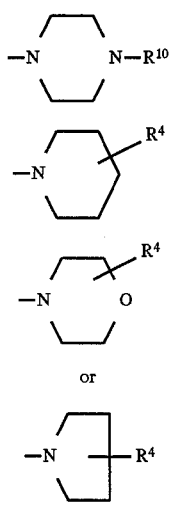

where R⁴ is as defined above and R¹⁰ is hydrogen, $C_1$–$C_4$ alkyl,

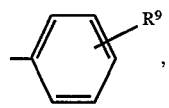

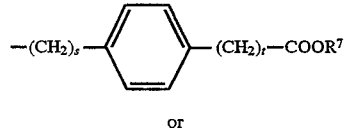

or

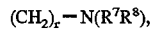

where R⁷, R⁸, R⁹ and r are as defined above and s and t are each independently an integer from 0 to 4, both inclusive; with the proviso that both m and n cannot be zero.

DETAILED DESCRIPTION OF THE INVENTION

As used herein, the term "$C_1$–$C_8$ alkyl" refers to straight and branched chain aliphatic radicals of 1 to 8 carbon atoms, both inclusive, such as methyl, ethyl, propyl, isopropyl, butyl, isobutyl, sec-butyl, tert-butyl, n-pentyl, isopentyl, n-hexyl, isohexyl, n-heptyl, n-octyl, isooctyl and the like. The term "$C_1$–$C_8$ alkyl" includes within its definition the terms "$C_1$–$C_6$ alkyl" and "$C_1$–$C_4$ alkyl".

The term "$C_1$–$C_6$ alkoxy" refers to the alkyl radicals of 1 to 6 carbon atoms, both inclusive, attached to the remainder of the molecule by oxygen and includes methoxy, ethoxy, propoxy, isopropoxy, butoxy, isobutoxy, sec-butoxy, tert-butoxy, pentoxy, hexoxy and the like.

The term "$C_2$–$C_8$ alkenyl" refers to straight and branched chain radicals of 2 to 8 carbon atoms, both inclusive, having a double bond. As such, the term includes ethylene, propylene, isopropylene, 1-butene, 2-butene, methyl-1-propene, 1-pentene, 2-pentene, 2-methyl-2-butene, 1-heptene, 1-octene and the like. The term "$C_2$–$C_8$ alkenyl" includes within its definition the term "$C_2$–$C_6$ alkenyl".

The term "$C_2$–$C_8$ alkynyl" refers to straight and branched chain radicals of 2 to 8 carbon atoms, both inclusive, having a triple bond. As such, the term includes acetylene, propyne, 1-butyne, 2-butyne, 1-pentyne, 2-pentyne, 3-methyl-1-butyne, 1-hexyne, 2-hexyne, 3-hexyne, 1-heptyne, 1-octyne and the like. The term "$C_2$–$C_8$ alkynyl" includes within its definition the term "$C_2$–$C_6$ alkynyl".

The term "$C_3$–$C_8$ cycloalkyl" refers to saturated alicyclic rings of 3 to 8 carbon atoms, both inclusive, such as cyclopropyl, methylcyclopropyl, cyclobutyl, cyclopentyl, cyclohexyl, cyclooctyl and the like.

The term "naphthyl" refers to a 1-naphthyl or 2-naphthyl moiety.

The term "halo" refers to bromo, chloro, fluoro and iodo.

The pharmaceutically acceptable salts of the compounds of formula I are also useful in treating multiple sclerosis. Accordingly, such salts are included within the scope of the method of this invention.

The term "pharmaceutically acceptable salt", as used herein, refers to salts of the compounds of formula I which are substantially non-toxic to living organisms. Typical pharmaceutically acceptable salts include those salts prepared by reaction of the free base form of the compound of formula I with a pharmaceutically acceptable mineral or organic acid. Pharmaceutically acceptable mineral or organic acids commonly employed to form such salts include inorganic acids such as hydrochloric, hydrobromic, hydroiodic, nitric, sulfuric and phosphoric acid, as well as organic acids such as para-toluenesulfonic, methanesulfonic, oxalic, para-bromophenylsulfonic, carbonic, succinic, citric, benzoic, acetic, and related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, hydrochloride, hydrobromide, hydroiodide, acetate, nitrate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-2-sulfonate, p-toluenesulfonate, mandelate and the like salts. Preferred pharmaceutically acceptable acid addition salts include those formed with mineral acids such as hydrochloric acid and nitric acid, and those formed with organic acids such as acetic acid, maleic acid, and methanesulfonic acid.

Depending upon the definitions of $R^3$, $R^4$ and n, the compounds of formula I may exist in various isomeric forms. This invention is not related to any particular isomer but includes all possible individual isomers and racemates. Unless otherwise indicated, all compounds named herein are intended to exist as racemic mixtures.

The phenols and benzamides of formula I are either known in the art or may be prepared by any of a number of well-known procedures. For example, many of the phenols of formula I may be prepared using Mannich reaction conditions. Such conditions are well known and essentially consist of condensing ammonia or a primary or secondary amine, with an aldehyde (especially formaldehyde) and an appropriately-substituted phenol.

The phenols of formula I may also be prepared using reductive amination. Such reaction entails reacting an appropriately substituted p-hydroxyphenylaldehyde (such as p-hydroxybenzaldehyde), or a ketone derivative thereof, with a primary amine so as to form an imine, which compound is then reduced with a reducing agent such as lithium aluminum hydride, sodium borohydride, sodium cyanoborohydride, hydrogen and a catalyst, or the like, to provide the corresponding amine. Reductive amination is an especially useful method for preparing the "dimer" compounds of formula I, i.e., those compounds wherein one of $R^5$ or $R^6$ is

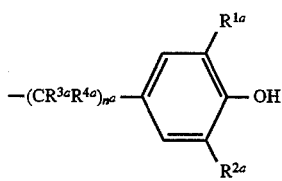

or

-continued

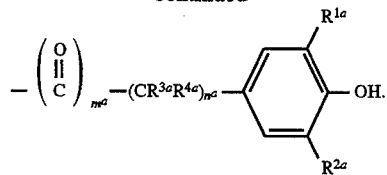

Such compounds are readily prepared by reductive amination provided the primary amine substrate is employed in a quantity sufficient to provide an amine/aldehyde or ketone mole ratio of less than about 3:1. If amine/aldehyde or ketone mode ratios of greater than about 3:1 are employed, the "monomer" (compounds wherein neither $R^5$ nor $R^6$ are as set forth immediately above) rather than the "dimer" are preferentially obtained.

Many of the benzamides of formula I may be prepared by reacting an appropriately substituted p-hydroxyphenylcarboxylic acid, such as p-hydroxybenzoic acid or p-hydroxybenzylcarboxylic acid, or a reactive derivative thereof (such as an acid chloride), with a primary or secondary amine to form the desired benzamide. When a free carboxylic acid substrate is employed, the reaction is usually carried out in the presence of a dehydrating agent such as 1,3-dicyclohexylcarbodiimide (DDC) or N,N-carbonyldiimidazole. The benzamide thus produced may be used in the method of treating multiple sclerosis of the present invention or, alternatively, may be converted to a phenol of formula I reduction of the amide functionality using a reducing agent such as lithium aluminum hydride, diborane or catalytic hydrogenation.

Phenols and benzamides of formula I wherein $R^1$ and/or $R^2$ are $C_2$-$C_6$ alkyl may also be prepared using Friedel-Crafts alkylation conditions. Such reaction conditions are well known and consist essentially of reacting a non-substituted or mono-substituted phenol or p-hydroxybenzamide of formula I (i.e., at least one of $R^1$ or $R^2$ must be hydrogen) with a $C_2$-$C_6$ alkene in the presence of a proton acid such as sulfuric acid.

A group of preferred compounds of formula I which are particularly suited for the method of the present invention are those compounds wherein $R^1$, $R^2$, $R^3$, $R^4$, m and n are as defined previously and $R^5$ and $R^6$ are defined to be one of the following:

A) $R^5$ and $R^6$ are each independently hydrogen, $C_1$-$C_6$ alkyl, $C_2$-$C_6$ alkenyl, $C_2$-$C_6$ alkynyl, —$(CH_2)_q$OH, —$(CH_2)_q$NH$_2$, —$(CH_2)_q$NH($C_1$-$C_4$ alkyl), —$(CH_2)_q$N($C_1$-$C_4$ alkyl)$_2$, —$(CH_2)_q$S($C_1$-$C_4$ alkyl) or

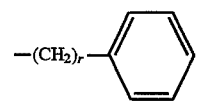

where q and r are both as previously defined;

B) one of $R^5$ and $R^6$ is as defined in (A) immediately above and the other is

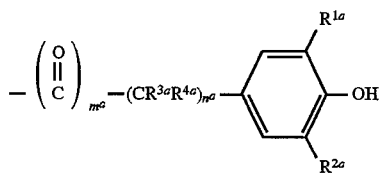

wherein $m^a$, $n^a$, $R^{1a}$, $R^{2a}$, $R^{3a}$ and $R^{4a}$ are the same substituent as m, n, $R^1$, $R^2$, $R^3$, and $R^4$, respectively; or C) $R^5$ and $R^6$, taken together with the nitrogen atom to which they are attached, form

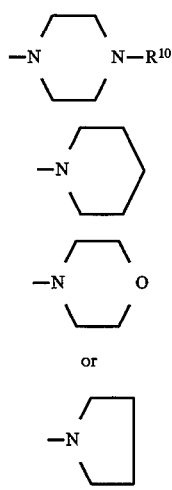

or wherein $R^{10}$ is hydrogen or $C_1$–$C_4$ alkyl.

In this preferred group of compounds, the following substituents are especially preferred.

i) $R^1$ and $R^2$ are each independently $C_1$–$C_4$ alkyl;
ii) one of $R^1$ and $R^2$ is 1,1-dimethylethyl and the other is $C_1$–$C_4$ alkyl;
iii) one of $R^1$ and $R^2$ is 1,1-dimethylethyl and the other is methyl;
iv) $R^1$ and $R^2$ are both 1,1-dimethylethyl;
v) one of $R^1$ and $R^2$ is 1,1-dimethylethyl and the other is hydrogen;
vi) one of $R^3$ and $R^4$ is hydrogen and the other is hydrogen or $C_1$–$C_4$ alkyl;
vii) one of $R^3$ and $R^4$ is hydrogen and the other is methyl;
viii) $R^3$ and $R^4$ are both hydrogen;
ix) n is 0 and m is 1;
x) n is 1 and m is 0;
xi) n is 2 and m is 0;
xii) $R^5$ and $R^6$ are each independently hydrogen or $C_1$–$C_6$ alkyl;
xiii) $R^5$ and $R^6$ are each independently hydrogen or $C_1$–$C_4$ alkyl;
xiv) $R^5$ and $R^6$ are each independently hydrogen or methyl;
xv) $R^5$ and $R^6$ are each independently hydrogen or ethyl;
xvi) $R^5$ and $R^6$ are each independently hydrogen or n-propyl;
xvii) $R^5$ and $R^6$ are each independently hydrogen or n-butyl;
xviii) $R^5$ and $R^6$ are each independently hydrogen or t-butyl;
xix) $R^5$ and $R^6$ are both methyl;
xx) $R^5$ and $R^6$ are both ethyl;
xxi) $R^5$ and $R^6$ are both n-propyl;
xxii) $R^5$ and $R^6$, taken together with the nitrogen atom to which they are attached, form

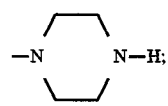

xxiii) $R^5$ and $R^6$, taken together with the nitrogen atom to which they are attached, form

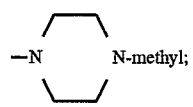

xxiv) $R^5$ and $R^6$, taken together with the nitrogen atom to which they are attached, form

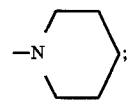

xxv) $R^5$ and $R^6$, taken together with the nitrogen atom to which they are attached, form

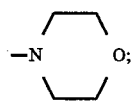

xxvi) $R^5$ and $R^6$, taken together with the nitrogen atom to which they are attached, form

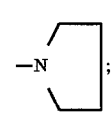

xxvii) pharmaceutically acceptable salts of any of the above compounds.

Especially preferred compounds which can be used in the method of the present invention are compounds of the formula

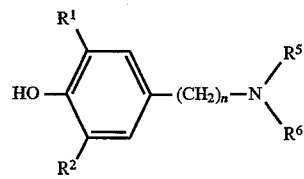

wherein $R^1$ and $R^2$ are either both 1,1-dimethylethyl or one of $R^1$ and $R^2$ is hydrogen or methyl and the other is 1,1-dimethylethyl, n is an integer from 1 to 4, both inclusive, and $R^5$ and $R^6$ are each independently hydrogen or $C_1$–$C_4$ alkyl or, when taken together with the nitrogen atom to which they are attached, form

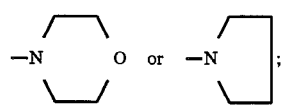

The most preferred compounds which may be used in the method of treating multiple sclerosis of the present invention include 4-[(dimethylamino)methyl]-2,6-bis(1,1-dimethylethyl)phenol, 4-(4-morpholinylmethyl)-2,6-bis(1, 1-dimethylethyl)phenol, 4-[2-(methylamino)ethyl]-2,6-bis(1,1-dimethylethyl)phenol, 4-[(methylamino)methyl]-2,6-bis(1,1-dimethylethyl)phenol, 4-[(ethylamino)methyl]-2,6-bis(1,1-dimethylethyl)phenol, 4-[2-(methylamino)ethyl]-2-(1,1-dimethylethyl)phenol and the pharmaceutically acceptable salts thereof.

Typical examples of compounds of formula I which are useful in treating multiple sclerosis according to this invention include:

4-[dimethylamino)methyl]-2,6-bis(1,1-dimethylethyl)phenol
4-[dimethylamino)methyl]-2,6-bis(1,1-dimethylethyl)phenol hydrochloride
4-[dimethylamino)methyl]-2,6-bis(1,1-dimethylethyl)phenol methanesulfonate
N,N-dimethyl-3,5-bis(1,1-dimethylethyl)-4-hydroxybenzamide
4-{[N-methyl-N-(4-hydroxy-3,5-bis(1,1-dimethylethyl)benzyl)amino]methyl}-2,6-bis(1,1-dimethylethyl)phenol
4-{[N-methyl-N-(4-hydroxy-3,5-bis(1,1-dimethylethyl)benzyl)amino]methyl}-2,6-bis(1,1-dimethylethyl)phenol hydrochloride
4-[2-dimethylamino)ethyl]-2,6-bis(1,1-dimethylethyl)phenol
4-[2-dimethylamino)ethyl]-2,6-bis(1,1-dimethylethyl)phenol hydrochloride
4-[2-methylamino)ethyl]-2,6-bis(1,1-dimethylethyl)phenol hydrochloride
4-(4-morpholinylmethyl)-2,6-bis(1,1-dimethylethyl)phenol
4-(4-morpholinylmethyl)-2,6-bis(1,1-dimethylethyl)phenol hydrochloride
4-(1-pyrrolidinomethyl)-2,6-bis(1,1-dimethylethyl)phenol
4-(1-pyrrolidinomethyl)-2,6-bis(1,1-dimethylethyl)phenol hydrochloride
4-[(N-ethyl-N-methylamino)methyl]-2,6-bis(1,1-dimethylethyl)phenol methanesulfonate
4-[(diethylamino)methyl]-2,6-bis(1,1-dimethylethyl)phenol hydrochloride
4-[(dipropylamino)methyl]-2,6-bis(1,1-dimethylethyl)phenol hydrochloride
4-[(methylamino)methyl]-2,6-bis(1,1-dimethylethyl)phenol hydrochloride
4-[(ethylamino)methyl]-2,6-bis(1,1-dimethylethyl)phenol hydrochloride
4-[(ethylamino)methyl]-2,6-bis(1,1-dimethylethyl)phenol nitrate
4-{[1,1-dimethylethyl)amino]methyl}-2,6-bis(1,1-dimethylethyl)phenol hydrochloride
4-[2-(methylamino)ethyl]-2-(1,1-dimethylethyl)phenol hydrochloride
4-[dimethylamino)methyl]-2-(1,1-dimethylethyl)-6-methylphenol
4-[(n-propylamino)methyl]-2,6-bis(1,1-dimethylethyl)phenol hydrochloride
4-[1-(ethylamino)ethyl]-2,6-bis(1,1-dimethylethyl)phenol hydrochloride
4-[(dipropylamino)methyl]-2,6-bis(1,1-dimethylethyl)phenol
4-[(N-ethyl-N-methylamino)methyl]-2,6-bis(1,1-dimethylethyl)phenol
4-[(diethylamino)methyl]-2,6-bis(1,1-dimethylethyl)phenol
4-[(n-propylamino)methyl]-2-ethylphenol
4-[(dimethylamino)methyl]-2,6-dimethylphenol
4-[(N-n-butyl-N-cyclohexylamino)methyl]-2,6-bis(1,1-dimethylethyl)phenol acetate
4-[3—(dicycloheptylamino)propyl]-2,6-diethoxyphenol
4-[2-(diphenylamino)ethyl]-2,6-diethylphenol tartrate
4-{4-[N-hexyl-N-(3-butene)amino]butyl}-2-methoxyphenol
4-{[(2-(dimethylamino)ethyl)amino]methyl}-2,6-diisopropylphenol hydrobromide
4-{[N-ethyl-N-(3-phenylpropyl)amino]methyl}-2-ethyl-6-methylphenol
4-{2-[N-cyclopentyl-N-(aminomethyl)amino]ethyl}-2-(1,1-dimethylethyloxy)phenol
4-{2-[2-hydroxyethyl)amino]ethyl}-2-propylphenol citrate
4-(1-piperidinylmethyl)-2,6-diethylphenol
4-(1-piperidinylmethyl)-2,6-diethylphenol hydrobromide
4-[1-(3-ethyl)piperidinylmethyl]-2,6-dimethoxyphenol
4-[4-(2-methyl)morpholinylmethyl]-2-(1,1-dimethylethyl)phenol phosphate
4-[2-(1-piperazinyl)ethyl]-2-n-butyl-6-methylphenol
4-{3-[1-(4-methyl)piperazinyl]propyl}-2-ethoxy-6-isopropylphenol toluenesulfonate
N-isopropyl-N-cyclobutyl-3,5-dimethyl-4-hydroxybenzamide hydrochloride
N-(methylthiomethyl)-3-(1,1-dimethylethyl)-4-hydroxybenzamide decanoate
N,N-diethylene-3-ethoxy-4-hydroxy-5-isopropylbenzamide maleate
(−)-4-[1-(methylamino)ethyl]-2,6-diethylphenol
(+)-4-[1-(diethylamino)butyl]-2-methoxyphenol lactate
(+)-4-[1-methyl-2-(cyclohexylamino)butyl]-2-isopropyl-6-methylphenol sulfate
(−)-4-[1-[1-(4-n-propyl)piperazinyl]ethyl]-2-ethoxy-6-methoxyphenol hydroxybenzoate
(−)-4-[1-(2-phenylethylamino)propyl]-2,6-bis(1,1-dimethylethyl)phenol sulfite
N,N-diethyl-[3-(3,5-diethyl-4-hydroxyphenyl)propyl]carboxamide
N-octyl-[(3-isopropyl-4-hydroxyphenyl)methyl]carboxamide heptanoate
N-methyl-N-n-propyl-[2-(3,5-diisobutoxy-4-hydroxyphenyl)ethyl]carboxamide formate
N-2-chlorophenyl-3,5-bis(1,1-dimethylethyl)-4-hydroxybenzamide
4-[(isopropylamino)methyl]-2,6-bis(1,1-dimethylethyl)phenol
4-[(isopropylamino)methyl]-2,6-bis(1,1-dimethylethyl)phenol hydrochloride As noted previously, the compounds of formula I are useful for treating multiple sclerosis. Such activity was demonstrated in the following test system.

EXPERIMENTAL AUTOIMMUNE ENCEPHALOMYELITIS (EAE) MODEL

Experimental autoimmune encephalomyelitis (EAE) is an inflammatory autoimmune demyelinating disease which can be induced in laboratory animals by injection of myelin basic protein. Such disease has become the standard laboratory model for studying clinical and experimental autoimmune diseases. In fact, numerous articles [e.g., Abramsky, et. al., *J. Neuroimmunol.*, 2, 1 (1982) and Bolton et al., *J. Neurol. Sci.*, 56 147 (1982)] note that the similarities of chronic relapsing EAE in animals to multiple sclerosis in humans especially implicates the value of EAE for the study of autoimmune demyelinating diseases such as multiple sclerosis. As such, the EAE test model was employed to establish the activity of the compounds of formula I against multiple sclerosis. Such testing was conducted according to the following procedure.

Female Lewis rats (Olac Ltd., U.K.), were injected in their footpads with 12.5 µg of myelin basic protein (MBP) (prepared form guinea-pig spinal cord) in Complete Freunds adjuvant. Test compound {4-[(dimethylamino)methyl]-2,6-bis(1,1-dimethylethyl)phenol} was given daily from day 0 (MBP injection date) in carboxymethylcellulose p.o. at various concentrations to the test animals. A control solution (carboxymethylcellulose alone) was given to certain other test animals. The animals were then weighed and scored daily for symptoms of EAE according to a scale of 0 to 3 (0=no change; 1=flaccid tail; 2=hind limb disability and 3=hind quarter paralysis/moribund). Animals were sacrificed when they reached a score of 3.

The results of the experiment described above are set forth in Table I, below. In Table I, Column 1 indicates whether the results reported are for test compound or control. Column 2 indicates the concentration of test compound employed. Columns 3–17 report the EAE disease score associated with various times after the MBP injection date (day 0).

for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate and mineral oil. The formulations can additionally include lubricating agents, wetting agents, emulsifying and suspending agents, preserving agents, sweetening agents or flavoring

TABLE I

Inhibition of EAE

| Test Compound/ Control | Dose of Test Compound (mg/Kg) | EAE Disease Score At Various Days After MBP Administration* | | | | | | | | | | | | | |
|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 |
| Control | — | 0 | 0 | 0 | 0 | 0 | 0 | 0 | 0 | 0 | .2 | 1.0 | 2.2 | 3.0 | 3.0 | 3.0 |
| Test Compound | 10 | 0 | 0 | 0 | 0 | 0 | 0 | 0 | 0 | 0 | 0 | 1.4 | 1.8 | 2.2 | 3.0 | 3.0 |
| Test Compound | 33 | 0 | 0 | 0 | 0 | 0 | 0 | 0 | 0 | 0 | 0 | 0 | .8 | 2.2 | 2.4 | 2.4 |
| Test Compound | 100 | 0 | 0 | 0 | 0 | 0 | 0 | 0 | 0 | 0 | 0 | 0 | 0 | 0.2 | 1.4 | 2.8 |

*EAE Disease Score based on an average of 5 test animals.

The results set forth in Table I, above, establish that the compounds of formula I inhibit the progression of EAE. In particular, at a dose of 33 mg/kg 4-[(dimethylamino)methyl]-2,6-bis(1,1-dimethylethyl)phenol delayed onset of the disease for at least 1 day relative to control. Dosages of 100 mg/kg of such compound delayed onset of EAE even further. As such, the data set forth in Table I establishes that the compounds of formula I would be expected to be efficacious in treating multiple sclerosis.

As noted above, the compounds of formula I are capable of slowing the process of neurodegeneration associated with multiple sclerosis, thereby lending themselves to the valuable therapeutic method claimed herein. This method comprises administering to a mammal in need of treatment for multiple sclerosis an amount of one or more compounds of formula I sufficient to achieve the therapeutic effect desired. The compounds can be administered by a variety of routes including the oral, rectal, transdermal, subcutaneous, intravenous, intramuscular or intranasal routes. The oral and transdermal routes of administration are preferred. No matter what route of administration is chosen, such administration is accomplished by means of pharmaceutical compositions which are prepared by techniques well known in the pharmaceutical sciences.

In making the pharmaceutical compositions, one or more active ingredients will usually be mixed with a carrier, or diluted by a carrier, or enclosed within a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium agents. The compositions may be formulated so as to provide rapid, sustained or delayed release of the active ingredient after administration to the patient by employing procedures well known in the art.

The compositions are formulated, preferably in a unit dosage form, such that each dosage contains from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with one or more suitable pharmaceutical diluents, excipients or carriers.

The compounds utilized in the method of the present invention are effective over a wide dosage range for the treatment of multiple sclerosis. Thus, as used herein, the term "therapeutically effective amount" refers to a dosage range of from about 0.5 to about 500 mg/kg of body weight per day. In the treatment of adult humans, the range of about 1 to about 100 mg/kg, in single or divided doses, is preferred. However, it will be understood that the amount of the compound actually administered will be determined by a physician, in the light of the relevant circumstances including the choice of compound to be administered, the chosen route of administration, the age, weight, and response of the individual patient, and the severity of the patient's symptoms, and therefore the above dosage ranges are not intended to limit the scope of the invention in any way.

The following formulation examples may employ as active ingredients any of the compounds of formula I. The examples are illustrative only and are not intended to limit the scope of the invention in any way.

EXAMPLE 1

Hard gelatin capsules are prepared using the following ingredients:

|  | Quantity (mg/capsule) |
|---|---|
| 4-[(dimethylamino)methyl]-2,6-bis(1,1-dimethylethyl)-phenol hydrochloride | 250 |
| Starch dried | 200 |
| Magnesium | 10 |

The above ingredients are mixed and filled into hard gelatin capsules in 460 mg quantities.

EXAMPLE 2

A tablet formula is prepared using the ingredients below:

|  | Quantity (mg/tablet) |
|---|---|
| 4-[(ethylamino)methyl]-2,6-bis(1,1-dimethylethyl)-phenol hydrochloride | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 3

An aerosol solution is prepared containing the following components:

|  | Weight % |
|---|---|
| 4-[2-(dimethylamino)ethyl]-2,6-bis(1,1-dimethylethyl)-phenol | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

EXAMPLE 4

Tablets each containing 60 mg of active ingredient are made up as follows:

|  |  |
|---|---|
| 4-[(dimethylamino)methyl]-2,6-bis(1,1-dimethylethyl)-phenol hydrochloride | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate and talc, previously passed through a No. 60 mesh U.S. Sieve, are then added to the granules which, after mixing, are compressed by a tablet machine to yield tablets each weighing 150 mg.

EXAMPLE 5

Capsules each containing 80 mg of medicament are made as follows:

|  |  |
|---|---|
| 4-[(methylamino)methyl]-2,6-bis(1,1-dimethylethyl)-phenol hydrochloride | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 6

Suppositories each containing 225 mg of active ingredient are made up as follows:

|  |  |
|---|---|
| 4-[2-(methylamino)ethyl]-2,6-bis(1,1-dimethylethyl)-phenol hydrochloride | 225 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 7

Suspensions each containing 50 mg of medicament per 5 ml dose are made as follows:

|  |  |
|---|---|
| 4-[(dimethylamino)methyl]-2,6-bis(1,1-dimethylethyl)-phenol hydrochloride | 50 mg |
| Sodium carboxymethylcellulose | 50 mg |
| Syrup | 1.25 ml |
| Benzoic acid solution | 0.10 ml |
| Flavor | q.v. |

| | |
|---|---|
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

EXAMPLE 8

Capsules each containing 150 mg of medicament are made up as follows:

| | |
|---|---|
| 4-[(dimethylamino)methyl]-2,6-bis(1,1-dimethylethyl)-phenol hydrochloride | 150 mg |
| Starch | 164 mg |
| Microcrystalline cellulose | 164 mg |
| Magnesium stearate | 22 mg |
| Total | 500 mg |

The active ingredient, cellulose, starch and magnesium stearate are blended, passed through a No. 45 mesh U.S. sieve, and filled into hard gelatin capsules in 500 mg quantities.

We claim:

1. A method of treating multiple sclerosis in a mammal in need of such treatment which comprises administering to said mammal a therapeutically effective amount of a compound, or a pharmaceutically acceptable salt thereof, of formula (I)

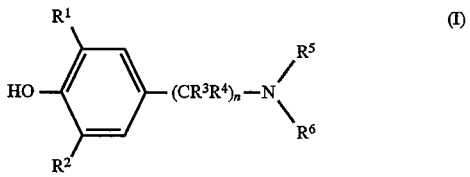

wherein:

$R^1$ and $R^2$ are each independently hydrogen, $C_3$–$C_6$ alkyl, $C_1$–$C_6$ alkoxy or $R^3$ and $R^4$ are each independently hydrogen or $C_1$–$C_4$ alkyl;

n is an integer from 0 to 4, both inclusive; and $R^5$ and $R^6$ are each independently hydrogen, $C_1$–$C_8$ alkyl, $C_3$–$C_8$ cycloalkyl, $C_2$–$C_8$ alkenyl, $C_2$–$C_8$ alkynyl, —$(CH_2)_qOR^7$, —$(CH_2)_qN(R^7R^8)$, —$(CH_2)_qSR^7$, —$(CH_2)_r$ naphthyl or

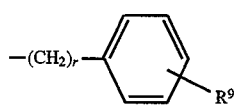

where q is an integer from 1 to 6, both inclusive, $R^7$ and $R^8$ are each independently hydrogen or $C_1$–$C_4$ alkyl, $R^9$ is hydrogen, halo, $C_1$–$C_4$ alkyl, trifluoromethyl, hydroxy, amino, $C_1$–$C_4$ alkylamino, di($C_1$–$C_4$ alkyl)amino, phenylamino or diphenylamino, and r is an integer from 0 to 4, both inclusive.

2. The method of claim 1 which employs a compound of formula I or a pharmaceutically acceptable salt thereof, wherein:

$R^1$ and $R^2$ are hydrogen or $C_3$–$C_6$ alkyl;

$R^5$ and $R^6$ are hydrogen, $C_1$–$C_6$ alkyl, $C_3$–$C_8$ cycloalkyl, $C_2$–$C_6$ alkenyl, $C_2$–$C_6$ alkynyl or

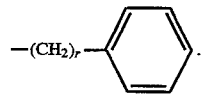

3. The method of claim 2 which employs a compound of formula I, or a pharmaceutically acceptable salt thereof, wherein $R^1$ and $R^2$ are either both 1,1-dimethylethyl or one of $R^1$ and $R^2$ is hydrogen and the other is 1,1-dimethylethyl, n is an integer from 1 to 4, both inclusive, $R^3$ and $R^4$ are hydrogen and $R^5$ and $R^6$ are each independently hydrogen or $C_1$–$C_4$ alkyl.

4. The method of claim 3 wherein the compound employed is 4-[(dimethylamino)methyl]-2,6-bis(1,1-dimethylethyl)phenol or a pharmaceutically acceptable salt thereof.

5. The method of claim 4 wherein the pharmaceutically acceptable salt thereof is the hydrochloride salt.

6. The method of claim 4 wherein the pharmaceutically acceptable salt thereof is the methanesulfonate salt.

7. The method of claim 3 wherein the compound employed is 4-[2-(methylamino)ethyl]-2,6-bis(1,1-dimethylethyl)phenol or a pharmaceutically acceptable salt thereof.

8. The method of claim 7 wherein the pharmaceutically acceptable salt thereof is the hydrochloride salt.

9. The method of claim 3 wherein the compound employed is 4-[(methylamino)methyl]-2,6-bis(1,1-dimethylethyl)phenol or a pharmaceutically acceptable salt thereof.

10. The method of claim 9 wherein the pharmaceutically acceptable salt thereof is the hydrochloride salt.

11. The method of claim 3 wherein the compound employed is a [(ethylamino)methyl]-2,6-bis(1,1-dimethylethyl)phenol or a pharmaceutically acceptable salt thereof.

12. The method of claim 11 wherein the pharmaceutically acceptable salt thereof is the hydrochloride salt.

13. The method of claim 3 wherein the compound employed is 4-[2-(methylamino)ethyl]-2-(1,1-dimethylethyl)phenol or a pharmaceutically acceptable salt thereof.

14. The method of claim 13 wherein the pharmaceutically acceptable salt thereof is the hydrochloride salt.

15. The method of claim 1 which employs a compound of formula I, or a pharmaceutically acceptable salt thereof, wherein:

$R^5$ and $R^6$ are each independently hydrogen, $C_1$–$C_6$ alkyl, $C_2$–$C_6$ alkenyl, $C_2$–$C_6$ alkynyl, —$(CH_2)_qOH$, —$(CH_2)_qNH_2$, —$(CH_2)_qNH(C_1$–$C_4$ alkyl), —$(CH_2)_qN(C_1$–$C_4$ alkyl)$_2$, —$(CH_2)_qS(C_1$–$C_4$ alkyl) or

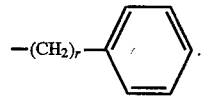

* * * * *

UNITED STATES PATENT AND TRADEMARK OFFICE
CERTIFICATE OF CORRECTION

PATENT NO.    : 5,633,283

DATED         : May 27, 1997

INVENTOR(S)   : Ann E. Kingston and Jill A. Panetta

It is certified that an error appears in the above-identified patent and that said Letters Patent is hereby corrected as shown below:

In Column 16, line 41, delete "[(ethylamino)methyl]" and insert therefor -- 4-[ (ethylamino) methyl] --.

Signed and Sealed this

Sixth Day of June, 2000

Attest:

Q. TODD DICKINSON

Attesting Officer    Director of Patents and Trademarks